United States Patent
Coluccia (10) Patent No.: US 10,765,479 B2
(45) Date of Patent: Sep. 8, 2020

(54) METHOD FOR TREATMENT OF VARICOCELE

(71) Applicant: biolitec Unternehmensbeteiligungs II AG, Vienna (AT)

(72) Inventor: Fabio Coluccia, Milan (IT)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 274 days.

(21) Appl. No.: 15/438,471

(22) Filed: Feb. 21, 2017

(65) Prior Publication Data
US 2018/0168728 A1    Jun. 21, 2018

Related U.S. Application Data

(63) Continuation-in-part of application No. 12/985,602, filed on Jan. 6, 2011, now Pat. No. 9,034,024, which
(Continued)

(51) Int. Cl.
*A61B 6/00* (2006.01)
*A61B 18/24* (2006.01)
(Continued)

(52) U.S. Cl.
CPC ............. *A61B 18/24* (2013.01); *A61B 6/12* (2013.01); *A61B 6/481* (2013.01); *A61B 6/504* (2013.01);
(Continued)

(58) Field of Classification Search
CPC ........... A61B 18/24; A61B 6/12; A61B 6/481; A61B 6/504; A61B 8/0841;
(Continued)

(56) References Cited

U.S. PATENT DOCUMENTS 4,509,504 A * 4/1985 Brundin ............... A61K 9/0039
128/831
5,167,624 A    12/1992 Butler
(Continued)

FOREIGN PATENT DOCUMENTS

WO        0166016        9/2001
WO    2009109967        9/2009

*Primary Examiner* — Michael W Kahelin
*Assistant Examiner* — Shirley X Jian
(74) *Attorney, Agent, or Firm* — Bolesh J. Skutnik; BJ Associates (57) ABSTRACT

A minimally invasive method for treating varices in especially sensitive areas, including pelvic varices in females, varicoceles, and also oesophageal varices is presented. The method comprises the steps of making a micro incision into the blood vessels of a patient, endoscopically inserting a catheter device into the blood vessel of a patient and advancing the distal end of the catheter to reach the varix or varices. Insertion can be made in the femoral vein and advanced using a catheter. A first localizer is placed on the distal end of said catheter to allow use of x-ray, angiography, or other imaging techniques to visualize and position the catheter. An optical fiber is then inserted into the catheter and the distal end is advanced to a predetermined point near the varix or varices. A second localizer is present on the distal end of said optical fiber to allow use of x-ray, angiography, or other imaging techniques to visualize and position the optical fiber as well. Optical fiber distal end is preferably a slim, radial 360 degree emitting fiber end. Laser energy of preferably 1470±30 nm is then transmitted to the varix to close the blood vessel. Other wavelengths with similar or greater absorption in blood/water than at 1470 nm are also effective. Imaging techniques such as angiographies may again be performed to confirm closure of the vein. The laser source linked to a radial emitting fiber allows for thermo occlusion of varicoceles using about 2-3 W of
(Continued)

emitting power with little or no pain or discomfort for patient. The present invention is an out-patient procedure that requires no anesthesia and minimal recovery time, and does not require that any foreign objects be left in the body. This method has been shown to have a high success rate and minimum pain or side effects for the patient.

13 Claims, 4 Drawing Sheets

Related U.S. Application Data is a continuation-in-part of application No. 11/637,377, filed on Dec. 12, 2006, now Pat. No. 8,257,411, which is a continuation-in-part of application No. 10/675,461, filed on Sep. 30, 2003, now abandoned.

(51) Int. Cl.
*A61B 8/08* (2006.01)
*A61B 6/12* (2006.01)
*A61B 18/00* (2006.01)
*A61B 90/00* (2016.01)

(52) U.S. Cl.
CPC ............ *A61B 8/0841* (2013.01); *A61B 8/488* (2013.01); *A61B 2018/00404* (2013.01); *A61B 2018/00982* (2013.01); *A61B 2090/376* (2016.02); *A61B 2090/378* (2016.02); *A61B 2090/3966* (2016.02); *A61B 2090/3983* (2016.02)

(58) Field of Classification Search
CPC ........ A61B 2090/376; A61B 2090/378; A61B 2090/3966; A61B 2090/3983; A61B 8/488; A61B 2018/00404; A61B 2018/00982; A61B 25/0105; A61M 2039/0045; A61M 25/0108; A61M 2025/09166; A61M 2025/1079

See application file for complete search history.

(56) References Cited

U.S. PATENT DOCUMENTS

| | | | |
|---|---|---|---|
| 6,200,332 B1 | 3/2001 | Del Giglio | |
| 7,524,316 B2* | 4/2009 | Hennings | A61B 18/24 |
| | | | 128/898 |
| 9,034,024 B2 | 5/2015 | Coluccia | |
| 9,962,215 B2* | 5/2018 | Shimizu | A61B 18/082 |
| 2002/0156499 A1 | 10/2002 | Konya | |
| 2002/0165450 A1* | 11/2002 | Sanchez | A61B 17/12113 |
| | | | 600/434 |
| 2004/0092913 A1* | 5/2004 | Hennings | A61B 18/24 |
| | | | 606/3 |
| 2005/0015123 A1* | 1/2005 | Paithankar | A61B 18/24 |
| | | | 607/88 |
| 2005/0131400 A1* | 6/2005 | Hennings | A61B 18/24 |
| | | | 606/15 |
| 2006/0217692 A1* | 9/2006 | Neuberger | A61B 18/24 |
| | | | 606/12 |
| 2008/0319376 A1* | 12/2008 | Wilcox | A61B 17/2202 |
| | | | 604/22 |
| 2009/0240242 A1 | 9/2009 | Neuberger | |
| 2010/0010476 A1* | 1/2010 | Galdonik | A61B 17/221 |
| | | | 604/529 |
| 2013/0116633 A1* | 5/2013 | Lichty, II | A61M 25/0043 |
| | | | 604/264 |
| 2015/0265332 A1* | 9/2015 | Shimizu | A61B 18/082 |
| | | | 606/29 |
| 2015/0265350 A1* | 9/2015 | Shimizu | A61B 17/12136 |
| | | | 606/14 |
| 2017/0119469 A1* | 5/2017 | Shimizu | A61B 18/22 |

* cited by examiner

METHOD FOR TREATMENT OF VARICOCELE

REFERENCE TO RELATED CASES

This application is a continuation-in-part of U.S. Pat. No. 9,034,024 filed on Jan. 6, 2011 by Coluccia et al., entitled "METHOD FOR TREATMENT OF VARICES", which in turn was based on the continuation in part of application Ser. No. 11/637,377, filed on Dec. 12, 2006, now U.S. Pat. No. 8,257,411, which is a continuation in Part of application Ser. No. 10/675,461 filed on Sep. 30, 2003, now abandoned, each of which is hereby expressly incorporated by reference in its entirety as part of the present disclosure.

BACKGROUND OF THE INVENTION

Field of the Invention

The invention relates to the field of treatment for male and female reproductive varices, in particular for varicoceles in men and pelvic varices in women, and includes oesophageal varices.

Information Disclosure Statement

Varices are uneven, permanent dilations of veins than can occur in numerous areas of the body, and are very common in the superficial veins of the lower limbs (varicose, spider veins). One manifestation of these varices that occurs in men, and is the most common cause of male infertility, is the varicocele. Between 10 and 20% of post-pubescent males are affected by varicoceles, and 20-40% of all infertile males have varicoceles. A varicocele specifically refers to dilatation and tortuosity of the pampiniform plexus. Pampiniform plexus is the network of veins that drain the testicle. Plexus travels along the posterior part of the testicle with the epididymis and vas deferens, and then into the spermatic cord, which extends from the testes up through the ingiunal canal in the lower abdominal wall to the circulatory system. The vas deferens is not situated by itself but is a part of a larger tissue bundle called the spermatic cord. The spermatic cord contains many blood vessels as well as the vas deferens, nerves, and lymphatic channels. Hence care needs to be taken to avoid vas deferens and vessels to avoided permanent damage to testis.

A varicocele can develop in one or both testicles, but in most cases occurs in the left testicle. Because of the varicocele's impairment of blood flow, the blood cannot cool as it does in normal veins, and this increased temperature is thought to be a cause of infertility. The excess heat can damage sperm or impede the production of new healthy sperm.

Varices can also play a role in chronic pelvic pain syndrome in women. One of numerous causes of chronic pelvic pain in women is "pelvic congestion syndrome" (PCS), a condition in which varices form in the pelvis minor, affecting organs including the uterus, ovaries and vulva. PCS is analogous to varicoceles in men. Pelvic varices occur in around 10% of the female population, and varices occur usually in women of the ages of 20-50.

A variety of treatments have been attempted for female pelvic varices, with varying degrees of success. Medications, including vasoconstrictors and hormonal medications, have been used successfully, though they may not always provide long-term relief. Numerous surgical treatments have also been performed, including tying off or removing veins, uterine suspension, and, generally as a last resort, hysterectomy.

Numerous options are also available for treatment of male varicoceles. Surgical treatment, usually performed under general anesthetic, involves making an incision above the scrotum and tying off the veins to detour blood flow into normal veins. Such a procedure can require up to six weeks recovery time before heavy lifting can be performed, with light activities able to be performed earlier.

Embolization is a procedure used by surgeons to block fluid flow through a blood vessel or organ, and has been used to treat both male varicoceles and female pelvic varices with at least some success. An embolus, which is a mass of some material, is inserted into the blood vessel with a catheter and is lodged in the vessel to restrict blood or fluid flow. This causes a clot to develop in the vessel that closes off the vessel. Types of emboli include wire coils, sponges, "chemical cross-linking means such as cyanoacrylate", balloons, umbrella-like devices and other types of plugs. (U.S. Pat. No. 5,167,624)

U.S. Pat. No. 4,509,504 discloses the use of a device consisting of a material that swells when in contact with body fluid. The device is inserted into a body passage and the material is swelled to occlude the passage. The passages could be blood vessels (including varicose veins), urethers, spermatic ducts and oviducts. The device can purportedly be used as a contraceptive. When swelled, the device anchors in position and fully occludes the passage.

U.S. Pat. No. 6,200,332 describes a device and method for underskin laser treatment. Indications such as wrinkles and varicose veins can be treated with this invention. The handpiece uses a standard needle to insert an optical fiber under the skin or into a blood vessel, and features an extension piece that maintains the end of the optical fiber in a fixed position relative to the handpiece. The method described in this invention is generally envisioned for the treatment of tissue near the surface of the skin, for cosmetic procedures such as surface varicose veins or wrinkle removal. It is not suitable for deep interior treatments such as varicoceles or pelvic varices because of the anatomical positions and function. Again because of the anatomical position of the vein care needs to be taken to avoid damages to renal arterial, like transection, intimal tears, or thrombotic occlusion U.S. Pat. No. 5,167,624 describes a method and apparatus for passing an embolus into a blood vessel. The embolus lodges in the vessel and allows formation of a vessel-occluding clot around the embolus. The embolus is hydraulically passed through the lumen of a catheter to a given point in a blood vessel; the hydraulic fluid pushed the embolus to a predetermined position in the blood vessel. The embolus is preferably a coil that is stretched in the catheter lumen and recoils once released into the blood vessels. The recoiling causes the spring to expand and exert a force on the wall of the blood vessel to anchor it in place.

U.S. Application No. 2002/0156499 describes an apparatus and method featuring a deformable member for occluding a blood vessel. Upon application of force on the occluder, the occluder can be deformed to expand to fully occlude a vessel, and may further be anchored so that migration can be avoided.

WO 01/66016 A1 describes embolic particles, agents and compositions, visible by ultrasound, for embolization to treat various disorders such as varicocele. Microbubbles are incorporated into or around the particles to allow the particles or composition to visible by ultrasound, thus avoiding the need for fluoroscopy and contrast agents in angiography.

Embolization procedures are typically outpatient procedures that require 24 hours or less of recovery time. Disadvantages include the relative complexity of the inserted embolus and the associated delivery equipment and the increased risk of infection, migration, or other complications due to the need to deposit and secure a foreign body within the blood vessel.

WO2009109967A1 discloses a method for collapsing a target vein comprising providing an intravascular irritation element having mechanical irritating objects, inserting the intravascular irritation element into a venous lumen of a target vein, and irritating the target vein by moving mechanical irritating objects in contact with the inner surface triggering a collapse of said target vein. Irritating objects include a shape memory element having a regainable geometry, wherein the providing comprises providing the intravascular irritation element in a collapsed state and the irritating comprises allowing the shape memory element to expand toward the regainable geometry in the venous lumen. Optionally, the irritating comprises rotating the intravascular irritation element around a longitudinal axis of the target lumen or brushing irritation element against the inner surface in a helical pattern. Inserting comprises releasing a sclerosing agent in proximity to the inner surface or withdrawing blood in proximity to the inner surface. Causing vein collapse by mechanical irritation lacks effectiveness and is often only a temporary benefit.

U.S. Pat. No. 9,034,024 discloses a method which comprises the steps of inserting a catheter device into the blood vessels of a patient and advancing the distal end of the catheter to reach the varix or varices. To visualize and position the catheter proper imaging techniques are used. The U.S. Pat. No. 9,034,024 mentions that the catheter is moved into position near the varicocele vein mass preferably under x-ray imaging.

Most of the procedures discussed in the prior art use invasive methods. Since varicoceles in men and pelvic varices in women are known to involve the reproductive organs extra care needs to be taken since most patients affected are in reproductive age group. The Pampiniform plexus in the testis and pelvis minor in pelvic regions, which are affected by varices are connected to other major veins, which are again connected to other vital organs in the abdominal cavity, and are surrounded by other major arteries and nerves in the regions, hence utmost care needs to be taken while accessing this vein unlike the veins in the legs. Any damage to the other veins or artery can cause significant, irreversible damage to reproductive organs.

In prior art cases the vein closure is not complete because collateral veins running parallel to testicular vein are missed, and recurrence is common. Collateral veins are difficult to identify and ligate separately from the testicular artery. Similarly access to the right internal spermatic vein is very difficult and requires significant time.

Disadvantages include long duration of the procedure, Seduction, failure to access the internal spermatic vein, radiation exposure and recurrent varicocele. And most importantly the success of these procedures is clearly dependent upon a high level of skill and experience of the interventional radiologist.

Additionally, in the prior approach by the current inventors, U.S. Pat. No. '024, multiple use of the catheter and generally the variability of mechanical locking systems may cause some problems related to the distal tip of the fiber being not positioned for optimal behavior and safety. Tolerances in marking distance needed from the fiber's distal tip to the mechanical lock, as well as wear of the mechanical lock can introduce undesirable variation of the relative positioning of the distal ends of the catheter and optical fiber. This in turn can create errors in application of the laser radiation or even create the potential danger of accidentally irradiating the catheter distal end.

There remains a need for a minimally invasive treatment of varicocele and other delicately placed abnormal veins that does not require the permanent or extended insertion of foreign objects and can be performed with a minimum of pain, without significant recovery time, and with better information of the relative positioning of the distal tip of the fiber relative to the distal tip of the catheter to improve reliability and safety of the procedure. The present invention addresses these needs.

OBJECTIVES AND BRIEF SUMMARY OF THE INVENTION

It is an object of the present invention to provide an improved method for treatment of varices.

It is another object of the present invention to provide a method for treatment of varices, particularly pelvic varices, varicoceles and oesophageal varices that is minimally invasive, does not require general anesthesia, and requires little or no time for patient recovery, and does not require the deposition of foreign objects in the body.

It is yet another object of the present invention to provide a method for treatment of pelvic varices, varicoceles, and oesophageal varices that renders optimal effective energy emission and absorption to achieve permanent vein closure.

It is a further object of the present invention to provide a system whose catheter and optical fiber distal ends are independently located at a treatment site.

Briefly stated, the present invention discloses a minimally invasive method for treating varices in especially sensitive areas, including pelvic varices in females, varicoceles, and also oesophageal varices. The method comprises the steps of making a micro incision into the blood vessels of a patient, endoscopically inserting a catheter device into the blood vessel of a patient and advancing the distal end of the catheter to reach the varix or varices. For treatment of male varicocele, insertion is preferably made directly at the testicle. Alternatively, insertion can be made in the femoral vein and advanced using a catheter. Preferably, x-ray, angiography, or other imaging techniques are used to visualize and position the catheter. An optical fiber is then inserted into the catheter and the distal end of the flexible optical fiber is advanced to a point near the varix or varices. As described for the catheter, preferably x-ray, angiography, or other imaging techniques are used to independently visualize and position the optical fiber as well. Optical fiber distal end is preferably a slim, radial 360 degree emitting fiber end. Laser energy of preferably 1470±30 nm is then transmitted to the varix to close the blood vessel. Other wavelengths with similar or greater absorption in blood/water than at 1470 nm are also effective. Imaging techniques such as angiographies may again be performed to confirm closure of the vein. The laser source linked to a radial emitting fiber allows for thermo occlusion of varicoceles using about 2-3 W of emitting power with little or no pain or discomfort for patient. The present invention is an out-patient procedure that requires no anesthesia and minimal recovery time, and does not require that any foreign objects be left in the body. This method has been shown to have a high success rate and minimum pain or side effects for the patient.

DETAILED DESCRIPTION OF PREFERRED EMBODIMENTS

U.S. Pat. No. 9,034,024 to Coluccia et al. which is hereby incorporated by reference in its entirety as part of the present disclosure, as noted in the priority section, relates to a method of treating varices, wherein a mechanical lock of the treating fiber to the catheter together with accurate positioning of the catheter distal end by imaging means is described. Imaging techniques such as angiographies are then performed to confirm closure of the vein. It is an out-patient procedure that requires no incision or general anesthesia, requires minimal recovery time, and does not require that any foreign objects be left in the body. The lack of independent location of the optical fiber distal end/tip leads to some problems described in the prior section. Moreover, recent experience revealed that continuous emission mode offers better results over pulsed emission modes when it comes to permanent vessel ablation.

The present invention is a method for treating male and female varices located in or near the reproductive system. Due to their anatomical location within the body their treatment is considered to be delicate when compared to leg veins and their treatment methods. Moreover the affected veins are connected to other veins which in turn are connected to vital organs in that region, hence this vein needs to be carefully treated to avoid irreversible damage to these organs and their function.

In particular, the method is effective for treating varicoceles in men and pelvic varices in women. It is an outpatient procedure performed under local anesthetics, it can be quickly performed with a minimum of recovery time, and avoids the need to introduce foreign objects into the body, in contrast to traditional embolization treatments.

A small catheter is inserted into the circulatory system either at the groin, preferably into the femoral vein. Preferably under x-ray imaging, the catheter is moved into position near the varicocele vein mass. Alternatively, in the case of male varicocele, entry can be made through a more direct percutaneous access above the scrotum at the base of the penis by making a small painless incision. Presently the catheter has a first localizer placed at least at its distal end. This first localizer could be a patch made of a material like tungsten, gold or platinum on the distal end of the catheter. Optionally, other visualization procedures may be used to achieve correct positioning of the catheter.

After the catheter is correctly positioned, the already mentioned flexible optical fiber is inserted into the catheter. The optical fiber and its distal end, having a second localizer, is advanced to a point near the varix or varices to be treated. An x-ray imaging technique is preferably used to visualize and position the distal end of the optical fiber. This second localizer could also be a patch made of a material like tungsten, gold or platinum at the distal end of the flexible optical fiber. The second localizer could also be a spiral wire of said material attached or alongside the distal end of the optical fiber. It is obvious that the localizer's measurements and placement is chosen in a way which minimizes affects on the emission of laser energy. In general these examples are not to be understood as a limitation since those skilled in the art are able to choose other materials as well without departing from the scope of the present invention. In another embodiment the flexible optical fiber could also be coated partly or over the entire length and circumference with barium sulfide, allowing the optical fiber to be detectable via x-ray.

Additionally other visualization procedures such as angiographies with contrast (dye) may be performed to achieve correct positioning of the optical fiber too. Upon completing the positioning of the catheter and the optical fiber at the treatment site, laser energy is then transmitted through the optical fiber to the varix to close the blood vessel. The proximal end of said flexible optical fiber is optically connectable to a source of radiation. Said radiation source is preferably selected from the group consisting of a diode laser and a diode laser array. Laser energy having a wavelength of preferably 1470±30 nm is then delivered following a preselected radiation protocol of parameters, which may vary according to each patient. Such protocol parameters include emission mode and emitted power. Preferably, settings are 2-3 Watts in continuous mode. Ideal pullback speed is approximately 0.25 cm per second.

Following irradiation, the catheter and the optical fiber are withdrawn together until their ends reach the proximal part of the varicocele vein. The fiber is withdrawn through the catheter and dye may be injected so that further angiographies can be performed to confirm the closure of the vein. Other visualization techniques, such as echo color Doppler ultrasound, may also be used.

Radiation is preferably delivered through a 400 μm, 360 radially emitting optical fiber, such as the one described in US Published Application, 2009/0240242 to Neuberger. A preferred radiation source is a 4 Watt diode laser or diode array emitting at a wavelength of 1470±30 nm. The optical fiber is connected to the radiation source at its proximal end and its distal end contains a means for distributing radiation. This radiation distribution means may take a variety of forms, preferably a 360 degree radial emitting distal end or alternatively a diffuser end is used. Laser energy, especially in the range of 1470±30 nm, is optimal for effecting vein closure by causing the vein wall to shrink and close off the vein, due to this wavelength's extremely high absorption by water. Damage to the vein wall creates a shrinking effect that acts to close from the vessel. The presence of blood in the vein plays a key role in evenly distributing thermal damage to the inner vein wall and creating damage over a wide inner surface area of the vein wall, and thus helps to more efficiently create a thrombotic occlusion and avoids simply cutting through the vein wall. This mechanism for closing the vein aids the collapse of the vessel wall due to the 1470 nm wavelength's high absorption in water within the blood. Additionally, the radiation can also have a coagulating effect on the blood, which can also aid in closing off or blocking the vein. Finally, radial emission greatly contributes to a fast and uniform radiation of vein walls. These effects may act in conjunction to cause effective closure of the vein.

An advantage of the present invention is that a foreign body need not be inserted into the vein to trigger embolization. Because of this, there is no need for a mechanism to push the embolus into the vein, which simplifies both the procedure and the equipment needed. In addition, because no foreign body is left in the vein after treatment, the present invention does not introduce the risk of infection present in traditional embolization techniques. Also, the risk of migration, inherent in many detached occluding devices, is eliminated with the present invention.

There are numerous additional advantages of the present invention over prior art treatments. The method of the present invention does not require more than a small incision (only large enough to insert the small catheter), resulting in faster recovery and no damage to other vessels or organs and no scaring. Each of these improvements is significant to the well being of the patients. The use of general anesthetics can be avoided. Data show higher success rate then embolization. Lastly, little or no recovery time is required and patients can resume activities faster than after normal surgery.

Figure 1:
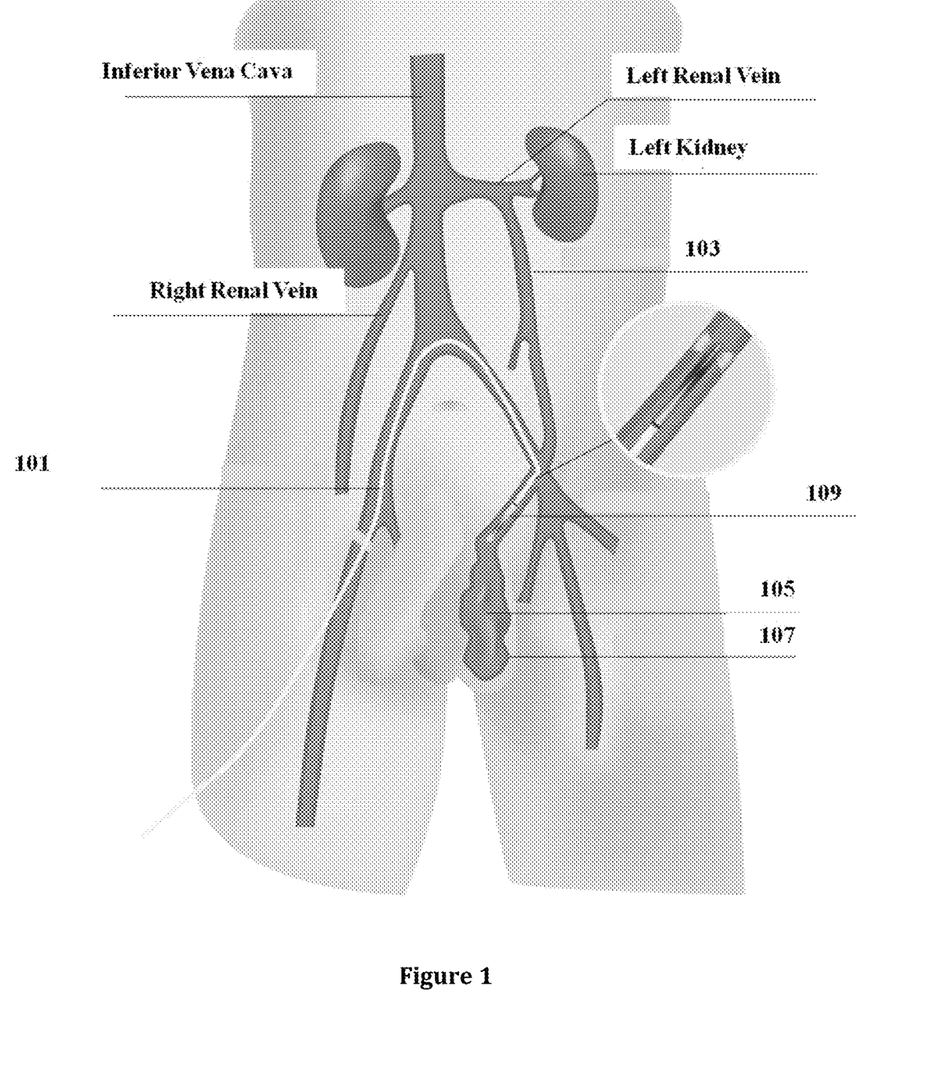
FIG. 1—Illustration of a preferred method for treatment of a varicocele.

A preferred embodiment of the present invention is illustrated in FIG. 1. In this embodiment, a varicocele above the left testicle is closed using radiation. Catheter (not shown) is inserted through the front of a patient's leg into the right femoral vein 101. The distal end of catheter is advanced through right femoral vein 101 and through left testicular vein 103 to a position near varicocele 105 above left testicle 107. Next, radial fiber 109 is inserted into catheter and advanced until distal end of fiber has reached a predetermined distance from the distal end of catheter. A radiation source is then activated and continuous 1470 nm laser radiation applied at 2-3 Watts closes off the veins of varicocele 105. Radial fiber 109 is then withdrawn and catheter may be withdrawn or used in an angiography to confirm that the varicocele has been effectively closed.

Figure 2:
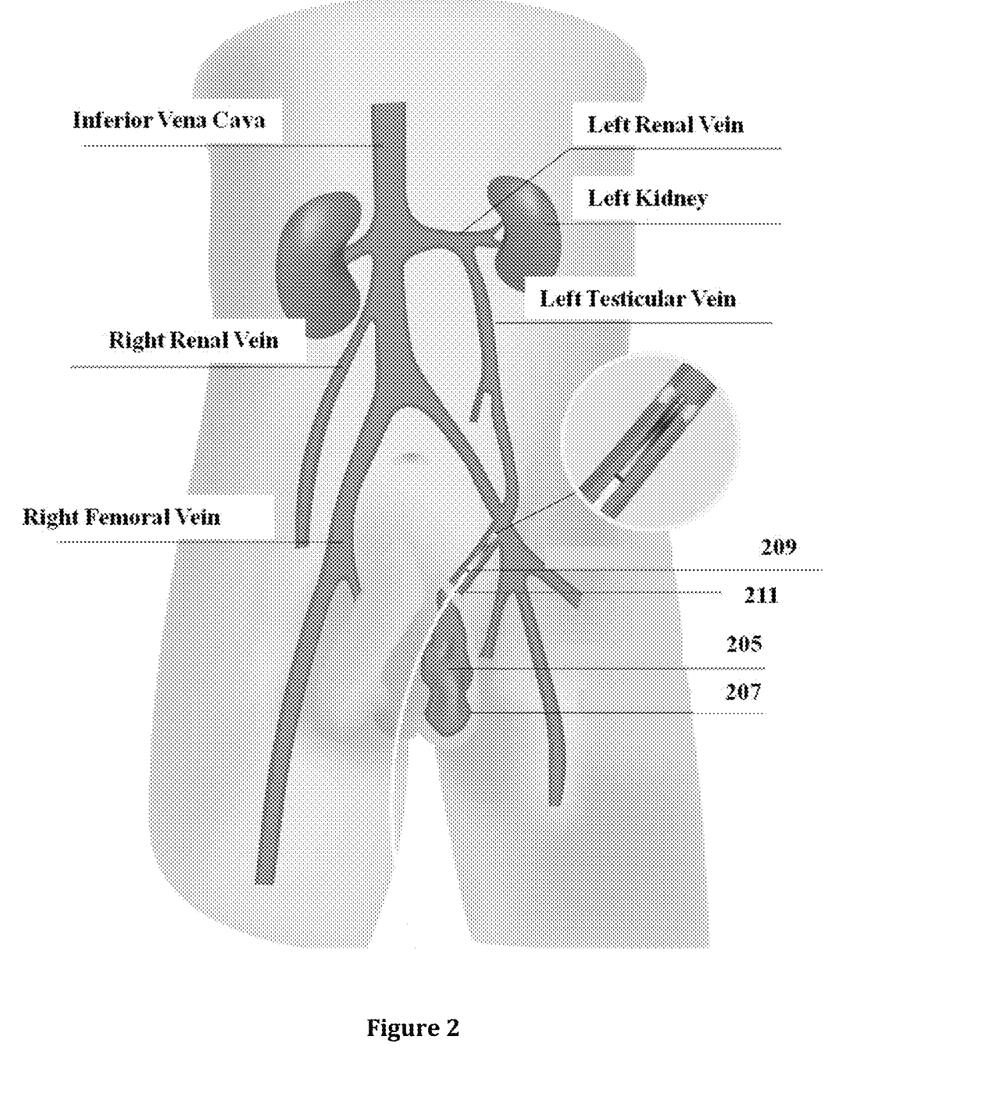
FIG. 2—Illustration of another preferred the method for treatment of a varicocele.

Another preferred embodiment of the present invention is illustrated in FIG. 2. In this embodiment a varicocele above the left testicle 207 is closed using radiation. A radial fiber 209 is inserted by ultrasound-guided percutaneous access above the scrotum 211 at the base of the penis to a position near varicocele 205 above left testicle 207. If necessary, saline water with anesthetic solution such as carbocaine or lidocaine 0.2% is applied at the point of percutaneous access. The radiation source is then activated and continuous 1470 nm laser radiation is applied at 4 Watts while withdrawing fiber 205. After verifying vein closure, radial fiber 209 is withdrawn.

Figure 5:
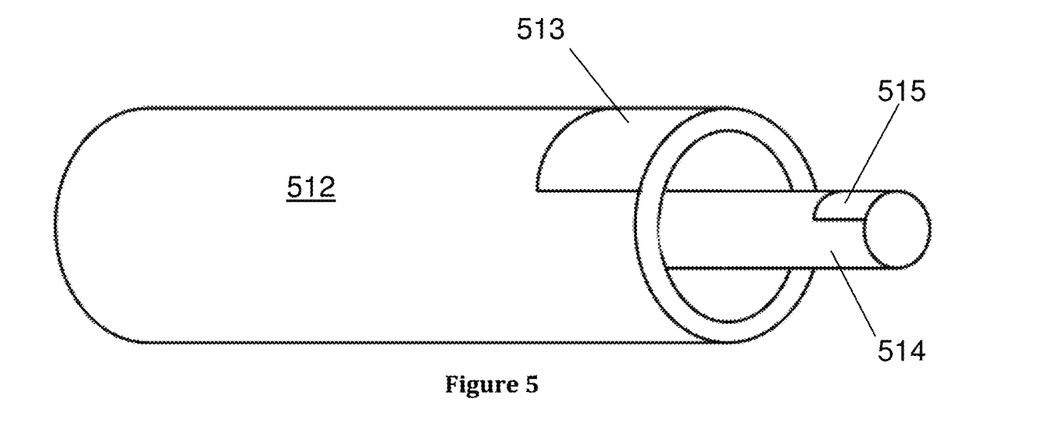
FIG. 5—schematic illustration of the distal ends of the catheter and optical fiber.

Another preferred embodiment of the present invention is illustrated in FIG. 5. On the distal end of catheter 512 first localizer 513 is placed. Optical fiber 514 has been lead through catheter 512. The distal end of optical fiber 514 extends beyond the distal end of catheter 512. On the distal end of optical fiber 514, second localizer 515 is situated. Both, first localizer 513 and second localizer 515 are detectable preferably by x-ray, so the position of each is independently viewable by using angiography.

The present invention is not merely limited to varicocele and female pelvic varices treatments and devices. Oesophageal varices, which also are delicate and difficult to treat because of their placement, may also be treated successfully using the method of the present invention. Oesophageal varices are enlarged veins on the lining of the esophagus that are prone to bleeding. They are life-threatening, and can be fatal in up to 50% of patients. They usually appear in patients with severe liver disease. For treatment of this indication, the method of the present invention is similar to that described above for varicoceles and female pelvic varices. In this embodiment, the catheter is inserted into the portal vein and advanced to a point proximate to the varices. Radiation as indicated above is applied to close off the vein.

The present invention is further illustrated by the following example, where a wavelength more commonly associated with tissue ablation or cutting is successfully used, but is not limited thereby.

Example 1

Figure 3:
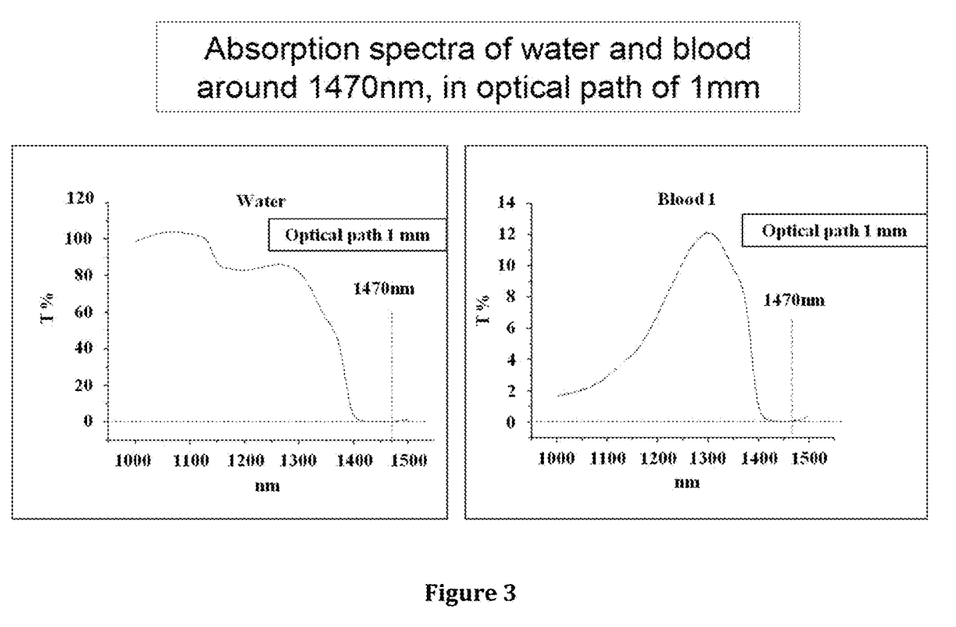
FIG. 3—Absorption spectra of water and blood around 1470 nm.
Figure 4:
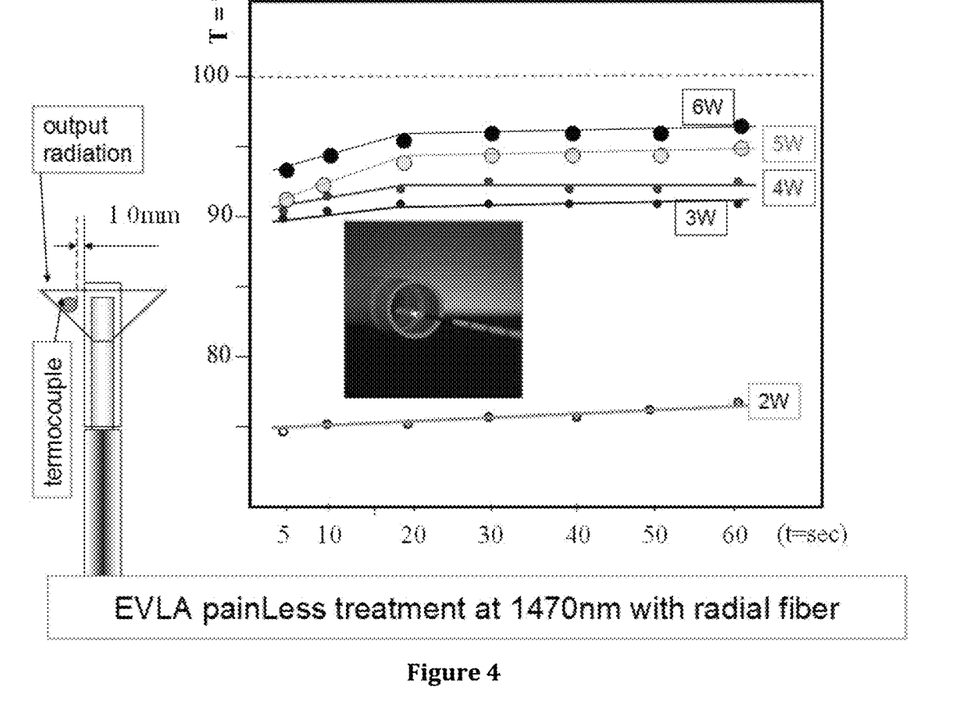
FIG. 4—Graph of measured temperatures at the radial fiber tip, immersed in water, using 1470 nm laser radiation at different power levels.

The present invention is very effective for treating varicoceles in the spermatic cord above the testicle. This example illustrates treatment of a varicocele above the left testicle of a patient. A catheter is inserted into the right femoral vein and advanced so that the distal end of the catheter is approximately 1 cm from the desired site of vein closure. As seen in FIG. 5, a first localizer placed at least at the distal end of the catheter allows using x-ray imaging and angiography to visualize this step and aid insertion. A 400 micron radial fiber is coupled to a 1470 nm diode laser, whose absorption in water and blood is nearly 100% as shown in FIG. 3, and then the fiber is advanced through the catheter until its distal end extends 2 cm from the distal end of the catheter. The optical fiber has a second localizer placed at her distal end as shown in FIG. 5. This allows following their way through the catheter using the x-ray imaging and angiography used for the visualization of the catheter for the optical fiber as well. Exact positioning of the tip of the optical fiber, independently from the catheter is thereby enabled. For most veins, the 1470 nm diode laser delivers a power of 2-3 W, in continuous wave (CW) mode. FIG. 4 shows a graph with the distribution of temperatures with the radial fiber immersed in water or blood, as a function of the output powers. If the diameter of the vein was greater than 6 mm, and its morphology is tortuous, the laser would need an output of up to 6 W in CW mode, to be similarly effective.

Having described preferred embodiments of the invention, with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A device for the treatment of varices, in the genital/pelvic area or in the oesophageal area, comprising:
   a) a catheter defining an elongated axis with a distal end receivable within a blood vessel;
   b) wherein at least one first localizer is placed at the distal end of said catheter, said first localizer being detectable by angiographic imaging;
   c) a flexible optical fiber defining an elongated axis, a proximal end optically connectable to a source of radiation, a distal end receivable within said catheter, and at least one second localizer placed at/near the distal end of said flexible optical fiber, said second localizer being detectable by angiographic imaging;
   d) wherein the distal end of said flexible optical fiber includes at least one radiation emitting surface configured to emit radiation reflected laterally with respect to the elongated axis of the flexible optical fiber and around the entire circumference of the flexible optical fiber onto a portion of a surrounding wall of said blood vessel in at least one axially extending annular beam; and e) whereby said first localizer allows determination of the position of the distal end of said catheter within said blood vessel by angiographic imaging and said second localizer allows independent determination of the position of the optical fiber distal end within said blood vessel and catheter by angiographic imaging.

2. The device for the treatment of varices according to claim 1, wherein said first and said second localizer are detectable by x-ray imaging.

3. The device for the treatment of varices according to claim 1, wherein said first and said second localizers consist of a metallic material.

4. The device for the treatment of varices according to claim 3, wherein said metallic material is selected from the group consisting of tungsten, platinum and gold.

5. The device for the treatment of varices according to claim 1, wherein either or both said first localizer and second localizer are shaped as spirals.

6. The device for the treatment of varices according to claim 1, wherein said optical fiber has a core diameter of 400 microns.

7. A device for the treatment of varices, comprising:
a) a catheter defining an elongated axis with a distal end receivable within the blood vessel;
b) wherein a first localizer detectable by angiographic imaging is placed at the distal end of said catheter;
c) a flexible optical fiber defining an elongated axis, a proximal end optically connectable to a source of radiation, a distal end receivable within said catheter, and having a second localizer detectable by angiographic imaging at the distal end of said optical fiber;
d) wherein the distal end of said flexible optical fiber includes a radiation emitting surface configured to emit radiation reflected laterally with respect to the elongated axis of the flexible optical fiber and around the entire circumference of the flexible optical fiber onto a portion of a surrounding wall of said blood vessel in an axially extending annular beam;
e) wherein said first localizer and said second localizer consist of a metallic material; and
f) wherein said first or second localizer is shaped as a spiral whereby said first localizer allows determination of the position of the distal end of said catheter within said blood vessel by angiographic imaging and said second localizer allows independent determination of the position of the distal end of said optical fiber within said blood vessel by angiographic imaging.

8. A method for the treatment of varices in the genital/pelvic area or in the oesophageal area, comprising the steps of:
a) inserting a catheter, with a distal end having at least one first localizer detectable by angiographic imaging, into a blood vessel, viewing the part of said distal end of the catheter utilizing angiographic imaging to locate the distal end of the catheter near the variovele vein mass;
b) inserting into said catheter a flexible optical fiber defining an elongated axis, whose proximal end is optically connectable to a source of radiation, whose distal end is receivable within said catheter, and whose distal end has at least one second localizer detectable by angiographic imaging;
c) advancing the distal end of said flexible optical fiber through said catheter to a predetermined point near said at least one varix while viewing the part of said distal end of the flexible optical fiber utilizing angiographic imaging to determine the location of the distal end of the optical fiber;
d) emitting radiation laterally with respect to the elongated axis of the flexible optical fiber and around the entire circumference of the flexible optical fiber in at least one axially extending annular beam, into the blood vessel;
e) irradiating blood within said varix with said radiation so as to cause closure of said at least one varix; and, wherein said angiographic imaging uses x-ray.

9. The method for treatment of varices according to claim 8, wherein said predetermined point is 1 cm beyond said distal end of said catheter.

10. The method for treatment of varices according to claim 8, wherein said radiation source is selected from the group consisting of a diode laser and a diode laser array wherein said radiation has a wavelength of 1470±30 nm.

11. The method for treatment of varices according to claim 8, wherein said irradiation step is accomplished by applying continuous radiation.

12. The method for treatment of varices according to claim 8, comprising the additional step of performing an additional angiography after said irradiation step to confirm closure of said varix.

13. The method for treatment of varices according to claim 8, comprising an additional step of utilizing echo color Doppler ultrasound to view a path of said catheter during said step a, catheter insertion.

\* \* \* \* \*